United States Patent [19]

Diana et al.

[11] Patent Number: 5,684,024
[45] Date of Patent: Nov. 4, 1997

[54] PYRAZOLE DIMERS COMPOSITIONS AND METHODS FOR TREATING INFLUENZA

[75] Inventors: Guy D. Diana, Pottstown; Dorothy C. Young, Collegeville; Tandy D. Goldstein, Norristown; Theodore J. Nitz, Pottstown; John Swestock, Pottstown; William P. Gorczyca, Pottstown, all of Pa.

[73] Assignee: Viropharma Incorporated, Malvern, Pa.

[21] Appl. No.: 645,164

[22] Filed: May 13, 1996

Related U.S. Application Data

[60] Provisional application No. 60/010,591, Jan. 25, 1996.

[51] Int. Cl.$^6$ .................. A61K 31/415; C07D 403/404; C07D 413/14
[52] U.S. Cl. .................. 514/364; 514/381; 514/404; 548/365.4; 548/131; 548/143; 548/253
[58] Field of Search .................. 548/365.4, 131, 548/143, 253; 514/364, 381, 404

[56] References Cited

U.S. PATENT DOCUMENTS

| | | | |
|---|---|---|---|
| 3,152,180 | 10/1964 | Haaf | 260/561 |
| 3,352,912 | 11/1967 | Prichard | 260/563 |
| 3,483,254 | 12/1969 | Shen et al. | 260/563 |
| 3,496,228 | 2/1970 | Hoover | 260/563 |
| 3,534,084 | 10/1970 | Narayanan et al. | 260/490 |
| 3,538,160 | 11/1970 | Dunn et al. | 260/563 |
| 3,592,934 | 7/1971 | Prichard | 424/325 |
| 3,867,149 | 2/1975 | Furuya et al. | 96/101 |
| 3,933,798 | 1/1976 | Curtis et al. | 260/239.9 |
| 4,187,255 | 2/1980 | Bader et al. | 260/239.9 |
| 4,960,686 | 10/1990 | Kawashima et al. | 430/522 |
| 5,139,930 | 8/1992 | Kadowaki et al. | 430/507 |
| 5,238,799 | 8/1993 | Usami et al. | 430/522 |
| 5,563,028 | 10/1996 | Nakamura et al. | 430/522 |

OTHER PUBLICATIONS

Hennig et al. J. Prakt. Chem. (1989), 331 (4), 584–90.
Schulz et al. J. Prakt. Chem./Chem.-Ztg. (1993), 335 (7), 607–15.
Nayak et al. J. Indian Chem. Soc. vol. LVII, (1980), pp. 643–645.
Trofimov et al. Translation from Zhural Analiticheskoi Khimii, vol. 37, No. 8, pp. 1445–1451, (1981).
Farouk et al. Zhurnal Fur Praktische Chemie. vol. 313, (6) (1971), pp. 1143–1147.
A.S. Galabov et al., Dokl. Bolg. Akad. Nauk, 43(5): 61–64 (1990).
A. Kreutzberger et al., Arch. Pharm. (Weinheim), 319: 18–25 (1986).
N.V. Trofimov et al., Zh. Anal. Khim., 37(8): 1113–1119 (1982).
M. Nayak et al., J. Indian Chem. Soc., 57(6): 643–645 (1980).

*Primary Examiner*—Mukund J. Shah
*Assistant Examiner*—Sabiha Qazi
*Attorney, Agent, or Firm*—Dann, Dorfman, Herrell and Skillman

[57] ABSTRACT

Substituted pyrazole dimers are useful in prophylaxis and treatment of influenza virus infections.

25 Claims, No Drawings

PYRAZOLE DIMERS COMPOSITIONS AND METHODS FOR TREATING INFLUENZA

This application claims the benefit of U.S. Provisional Application No. 60/010,591, filed Jan. 25, 1996.

FIELD OF THE INVENTION

The present invention relates to compounds, compositions and methods for the treatment of influenza infection. In particular, the present invention relates to novel pyrazole derivatives, pharmaceutical compositions containing such derivatives and their use in treating influenza infection and other viral diseases.

BACKGROUND OF THE INVENTION

There are three known influenza-type viruses which affect human beings: Influenza A, B and C. Influenza A viruses have been isolated from many animal species in addition to humans, while the influenza B and C viruses infect mainly humans. The influenza viruses are enveloped viruses containing negative single-stranded RNA's which are segmented and encapsidated. The influenza virus envelope is characterized by the presence of two surface glycoproteins: hemagglutinin and neuraminidase. The influenza A and B virions are pleomorphic and are usually 80–120 nm in diameter. The influenza C virion has many distinctive properties and is thus distinguished from the closely related A and B virions. Infection with influenza A or B often can cause a highly contagious, acute respiratory illness.

Influenza viruses have a major impact on morbidity leading to increases in hospitalization and in visits to health care providers. High rates of hospitalization are observed for patients over 65 years of age and also for children less than 5 years of age. Influenza virus is also unique among respiratory viruses in being a cause of excess mortality. Furthermore, the spread of influenza virus through a population can result in epidemics which have considerable economic impact. For example, high rates of mortality were observed due to influenza infection during the influenza epidemics of 1957, 1968 and 1977. *Fields Virology*, Second Edition, Volume 1, pp. 1075–1152 (1990).

There are relatively few known compounds that have significant anti-viral activity against influenza viruses. Two of these, amantadine and rimantadine are approved in the United States for the treatment of influenza virus disease. Both compounds are most effective when used prophylactically and influenza viruses develop resistance to both compounds rapidly. See U.S. Pat. No. 3,152,180 and 3,352,912. Other compounds reported to have activity against influenza viruses are disclosed in U.S. Pat. Nos. 3,483,254, 3,496,228, 3,538,160, 3,534,084 and 3,592,934.

Insofar as is known, pyrazole derivatives have not been previously reported as being useful for the treatment of influenza infection.

SUMMARY OF THE INVENTION

In accordance with one aspect, the present invention provides compounds, including tautomeric forms, of the following structure:

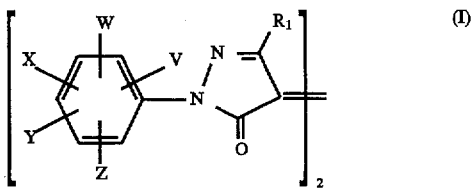

in which $R_1$ is R'CO, COOH, COOR'', $CONH_2$, $SO_2NH2$ or halogen; V is COOH, $CONH_2$, COOR''', $SO_2NH_2$ or

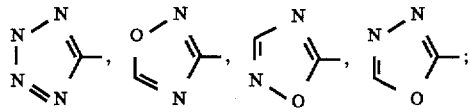

W, X, Y and Z represent the same or different substituents selected from the group of H, alkyl ($C_1$–$C_6$), halogen, $CF_3$, O-alkyl ($C_1$–$C_6$), COOH, COOR'''', $CH_3S$, $CH_3SO$, $CH_3SO_2$ and $CONH_2$, wherein R', R'', R''' and R'''' are alkyl ($C_1$–$C_6$) substituents. Included within the invention also are the pharmaceutically acceptable salts of the above compounds.

In accordance with another aspect, the present invention provides certain classes of intermediates which are useful in preparing compounds of formula I, above. One class of intermediate has the formula

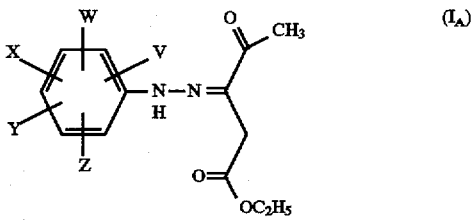

wherein V, W, X, Y and Z are as defined above. Another class of intermediate has the formula

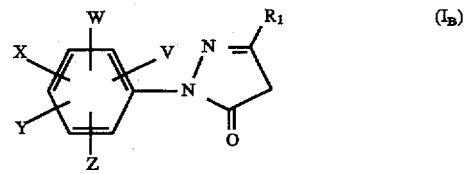

wherein $R_1$, V, W, X, Y and Z are as defined above.

According to still another aspect, the present invention provides pharmaceutical compositions comprising one or more of the above-described pyrazole derivatives in combination with a pharmaceutically acceptable carrier medium.

In accordance with yet another aspect, the present invention provides a method for treating viral influenza infections in mammalian hosts by administering an effective amount of the compounds of the invention to a patient susceptible to influenza infection or suffering from such an infection.

DETAILED DESCRIPTION OF THE INVENTION

The compounds of the invention can be conveniently prepared from known starting materials according to the general synthetic scheme illustrated below. Specific embodiments of anti-influenza compounds within the scope of the invention are exemplified below.

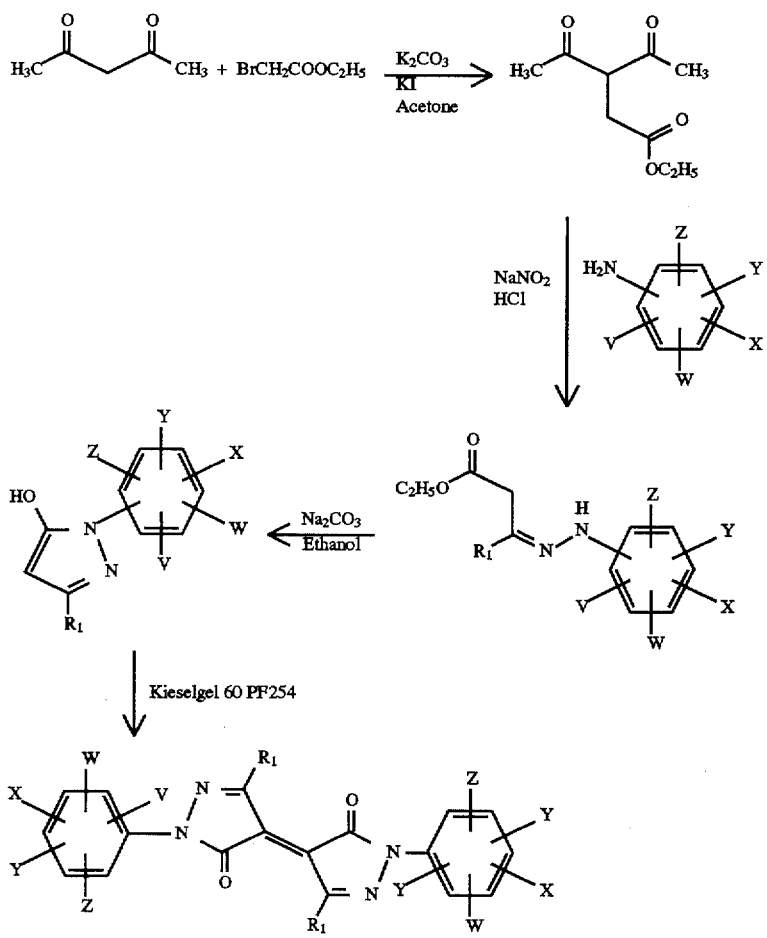

In vitro studies demonstrating the usefulness of the compounds of the invention as anti-viral agents against the influenza virus have been performed. Anti-viral activity was measured on the basis of the inhibition of influenza virus transcriptase and also as the reduction in plaque formation by the influenza virus. The biological studies of the anti-viral activity of the compounds of the invention are also described in the examples that follow.

Particularly good results have been obtained with compounds, including tautomeric forms, having the formula:

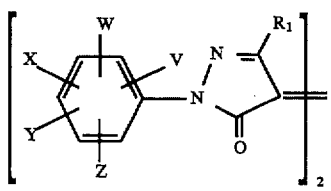

(II)

wherein $R_1$ represents $CH_3CO$; V represents a substituent selected from the group consisting of COOH, COOR, and $CONH_2$; W, X, Y and Z represent substituents selected from the group consisting of H, $CH_3$, $OCH_3$, COOH, COOR', $CH_3S$, $CH_3SO$, $CH_3SO_2$, $CONH_2$, or Cl, R and R' being the same or different lower alkyl group; and the pharmaceutically acceptable salts of said compound.

As previously noted, the compounds of formula I, above, including their pharmaceutically acceptable salts, exhibit antiviral activity against influenza virus.

The compounds of the invention can form basic salts with inorganic and organic bases, including, for example, alkali metal salts, such as Na or K salts, alkaline earth metal salts, such as Ca or Mg salts, ammonium, substituted ammonium and other amine salts such as morpholine, piperidine or pyridine salts.

The pharmaceutically acceptable salts of the compounds of formula I prepared following procedures which are familiar to those skilled in the art.

The compounds of the invention can exist in tautomeric forms such as the keto-enol tautomers. The tautomers occur naturally or under basic conditions.

The antiviral pharmaceutical compositions of the present invention comprise one or more of the compounds of formula I, above, as the active ingredient in combination with a pharmaceutically acceptable carrier medium or auxiliary agent.

The composition may be prepared in various form for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. In the pharmaceutical compositions of the invention, the active agent may be present in an amount of at least 0.5% and not more than 90% by weight based on the total weight of the composition, including carrier medium and/or auxiliary agent(s). Preferably, the proportion of active agent varies between 5%–50% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known carriers for medicaments may all be suitable as carrier media.

The compounds of the invention may be administered using any amount and any route of administration effective for attenuating infectivity of the influenza virus. Thus, the expression "amount effective to attenuate infectivity of influenza virus", as used herein, refers to a nontoxic but sufficient amount of the antiviral agent to provide the desired treatment of viral infection. The exact amount required will vary from subject to subject, depending on the species, age, and general condition of the subject, the severity of the infection, the particular antiviral agent and its mode of administration, and the like. The anti-influenza compounds are preferably formulated in dosage unit form for ease of administration and uniformity of dosage. Dosage unit form as used herein refers to a physically discrete unit of anti-viral agent appropriate for the patient to be treated. Each dosage should contain the quantity of active material calculated to produce the desired therapeutic effect either as such, or in association with the selected pharmaceutical carrier medium. Typically, the anti-viral compounds of the invention will be administered in dosage units containing from about 5 mg to about 500 mg of the anti-viral agent by weight of the composition with a range of about 50 mg to about 300 mg being preferred.

The compounds of the invention may be administered orally, parenterally, such as by intramuscular injection, intraperitoneal injection, aerosol, intravenous infusion or the like, depending on the severity of the infection being treated. The compounds of the invention may be administered orally or parenterally at dosage levels of about 0.1 to 50 and preferably from about 1 to about 25 mg/kg, of patient body weight per day, one or more times a day, to obtain the desired therapeutic effect.

Although the pyrazole derivatives described herein can be administered to any patient which is susceptible to influenza infection, the compounds are intended for the treatment of mammalian hosts, and especially humans.

The compounds of the invention will typically be administered from one to four times a day so as to deliver the above-mentioned daily dosage. However, the exact regimen for administration of the compounds and compositions described herein will necessarily be dependent on the needs of the individual patient being treated, the type of treatment administered and the judgment of the attending physician.

In view of the inhibitory effect on influenza virus transcriptase produced by the compounds of the invention, it is anticipated that these compounds will be useful not only for therapeutic treatment of infection, but for influenza viral prophylaxis, as well. The above-noted dosages will be essentially the same whether for treatment or prophylaxis of influenza infection.

The following examples are provided to describe the invention in further detail. These examples, which set forth the best mode presently contemplated for carrying out the invention, are intended to illustrate and not to limit the invention.

Examples 1 to 4 illustrate the chemical synthesis of one of the compounds of the invention. Keto-enol tautomers of the compounds of the invention are contemplated to be within the scope of the invention. Symmetrical and unsymmetrical compounds are also contemplated to be within the scope of the invention.

EXAMPLE 1

Preparation of Ethyl 3-acetyl-4-oxopentanoate

A solution of 28.2 ml (0.275 moles) of 2,4-pentanedione and 27.7 ml (0.25 moles) of ethyl bromoacetate in 50 ml of acetone was stirred under nitrogen while 38.0 g (0.275 moles) of dry potassium carbonate, predried at 100° C. under vacuum for 18 hours, was added. The mixture was heated to reflux for 4.5 hours. After cooling, the mixture was separated by filtration and the solid was washed with two portions of 50 ml of acetone. The filtrate was concentrated to dryness, dissolved in methylene chloride, filtered through Fluorosil, concentrated under vacuum to dryness, leaving a residual oil which was distilled. The fraction distilling at 48°–52° C. at 0.05 mm pressure was collected and 26.5 g of ethyl 3-acetyl-4-oxopentanoate were obtained.

EXAMPLE 2

Preparation of Ethyl 3-(4-carboxy-2-methylphenylhydrazono)-4-oxopentanoate

A mixture of 3 g (19.8 mmol) of 4-amino-3-methylbenzoic acid in 50 ml of water and 50 ml of ethanol and 3.56 ml of concentrated hydrochloric acid was cooled in an ice bath and then 1.5 g of $NaNO_2$ (21.8 mmol) in 10 ml of water was added portionwise. The mixture was allowed to come to room temperature and then added to a solution of 4.06 g (21.8 mmol) of ethyl 3-acetyl-4-oxopentanoate and 8 ml of pyridine in 25 ml of ethanol. The reaction mixture was left for 24 hr at room temperature with stirring. The mixture was acidified with concentrated hydrochloric acid and the mixture diluted with 20 ml of water. The resulting solid was collected and washed with water and pentane to yield 5.2 g of ethyl 3-(4-carboxy-2-methylphenylhydrazono)-4-oxopentanoate with m.p. 161°–162.5° C.

EXAMPLE 3

Preparation of 3-Methyl-4-(2-hydroxy-4-acetylpyrazolyl)-benzoic Acid

To a solution of 5 g (34 mmoles) of ethyl 3-(4-carboxy-2-methylphenylhydrazono)-4-oxopentanoate in 25 ml of ethanol and 25 ml of water was added with stirring 34.3 ml of a 1M sodium carbonate solution. The mixture was stirred at room temperature for 24 hr. The resulting mixture was acidified to pH 3 with 6M hydrochloric acid and the resulting solid was collected by filtration, washed with water and dried. The 3-methyl-4-(2-hydroxy-4-acetylpyrazolyl)-benzoic acid has a melting point of >250° C.

EXAMPLE 4

Preparation of 3,3'-Bis[3-Methyl-4-(2-hydroxy-4-acetylpyrazolyl)-benzoic Acid]

A mixture of 200 mg (0.69 mmol) Of 3-methyl-4-(2-hydroxy-4-acetylpyrazolyl)-benzoic acid and 7.5 g of silica gel (Kieselgel 60 PF254) were thoroughly mixed in a rotovap for 24 hr at room temperature. The mixture was suspended in 25 ml of a solution of 10 parts ethylacetate, 10 parts hexane and 5 parts acetic acid and filtered through a glass sintered filter. This procedure was repeated three times with the suspended solid and the material was finally washed with two portions of 25 ml of ethylacetate. The solid was then mixed in 25 ml of a solution containing 5 ml of aqueous saturated potassium carbonate solution and 20 ml of water and then filtered. This procedure was repeated three times after which time the filtrate was acidified and the solid separated by filtration. The solid was then washed repeatedly with water and then dried. 85 mg of dark solid was obtained.

The material was purified by reverse phase high pressure liquid chromatography by eluting isocratically with a solution containing 1 g of tetrabutylammonium dihydrogen phosphate, 2 ml of triethylamine in 1 liter of aqueous solution, and solution containing 1 g of tetrabutylammonium dihydrogen phosphate and 2 ml of triethylamine in a 1 liter methanolic solution. The material which eluted with a 50—50 mixture of each solution was collected, concentrated to dryness leaving a dark solid which was dissolved in water and the solution acidified with 6N hydrochloric acid. The resulting solid was collected, dissolved in water and passed through an ion exchange column containing 3 g of Bio-Rad resin:AG 50W-X8 (sodium ion form) and the column eluted with a 1:1 mixture of water and methanol. After removal of the solvents, 51 mg of dark solid was obtained. This material was characterized by NMR and chemical analysis.

By appropriate selection of aromatic amines, other products within the scope of the invention can be formed from the diazotization reaction. Particularly preferred are compounds having the structures given in the following table.

TABLE 1

| Example Number | Aromatic Amine | Product |
|---|---|---|
| 5 | HOOC—⟨⟩—NH₂, OCH₃ | HOOC—⟨⟩—N=N—C(COCH₃)=C(—C(O)—)C(=N—N—⟨⟩—COOH, OCH₃, H₃CO, H₃COC |
| 6 | HOOC—⟨⟩—NH₂, Cl | HOOC—⟨⟩—N=N—C(COCH₃)=C(—C(O)—)C(=N—N—⟨⟩—COOH, Cl, Cl, H₃COC |
| 7 | HOOC—⟨⟩—NH₂ | HOOC—⟨⟩—N=N—C(COCH₃)=C(—C(O)—)C(=N—N—⟨⟩—COOH, H₃COC |
| 8 | ⟨⟩—NH₂, HOOC | ⟨⟩—N=N—C(COCH₃)=C(—C(O)—)C(=N—N—⟨⟩—COOH, HOOC, HOOC, H₃COC |
| 9 | Cl—⟨⟩—NH₂, HOOC | Cl—⟨⟩—N=N—C(COCH₃)=C(—C(O)—)C(=N—N—⟨⟩—COOH, HOOC, Cl, H₃COC |

TABLE 1-continued

| Example Number | Aromatic Amine | Product |
|---|---|---|
| 10 | (structure) | (structure) |
| 11 | (structure) | (structure) |
| 12 | (structure) | (structure) |
| 13 | (structure) | (structure) |

Although the compounds prepared according to the foregoing examples are symmetric, unsymmetric compounds can also be similarly prepared. A proposed synthetic scheme for the preparation of unsymmetrical compounds is shown below. In this synthesis, the aryl-substituted acylated pyrazole starting material is halogenated e.g., using a suitable brominating agent. Next, the halogenated intermediate is coupled to an aryl-substituted acylated pyrazole different from the starting material, by means of a nucleophilic displacement reaction. Finally, the double bond between the two different moieties of the desired product is formed by an oxidation reaction.

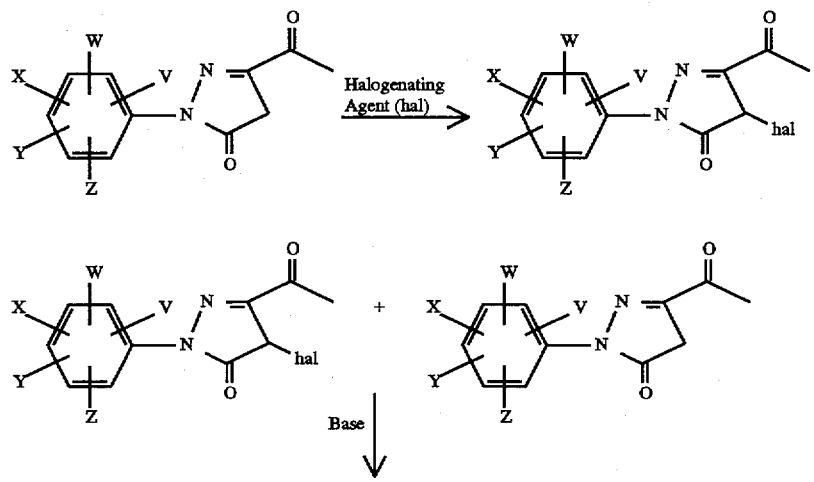

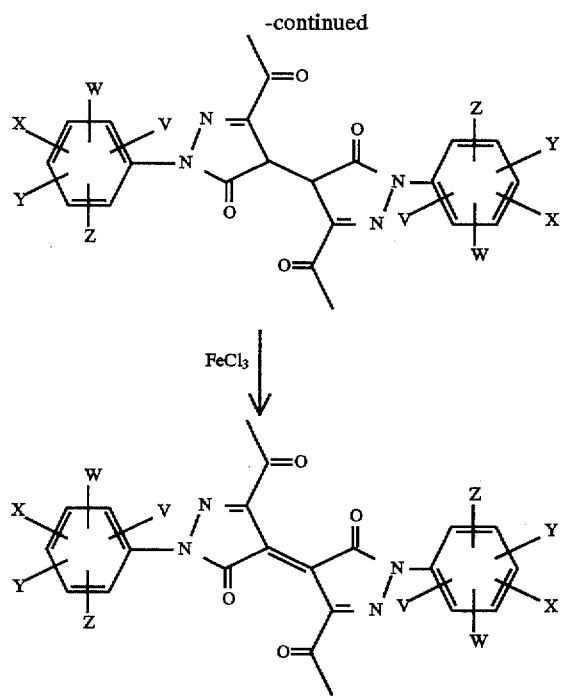

Examples 14 and 15 illustrate the efficacy of compounds of the invention in inhibiting the viral transcriptase activity and in inhibiting plaque formation by the virus.

EXAMPLE 14

Assay for Influenza A/WSN Virus Transcription

The assay for influenza A/WSN virus transcription was performed with detergent-treated purified influenza virions and 2'-O-methylated alfalfa mosaic virus RNA4 (A1MV RNA4) according to the following procedure. Duplicate reactions (50 µl in 96 well polypropylene U-bottom plates) contained 50 mM Hepes, pH 8, 50 mM potassium acetate, 5 mM dithiothreitol, 5 mM magnesium chloride, 1% Triton N-101, 35 µM ATP, 0.3 µM CTP, 0.5 µM GTP, 1 µM UTP, 2 µCi 35S-UTP (Amersham SJ1303), 0.75 µg (15 µg/ml) purified virions, and 5 ng (0.4 nM) cap 1 AlMV RNA4. Test compounds were solubilized with 100% dimethylsulfoxide (DMSO) and were present in the reactions at 1% DMSO. The reference standard inhibitor, poly (A,G), was present at concentrations of 10, 3, 1, 0.3, and 0.1 µg/ml. Incubation was for 45 min at 31° C. Reactions were stopped by the addition of 150 µl of ice-cold 7% trichloracetic acid (TCA) +2% sodium pyrophosphate containing 50 µg/ml yeast tRNA. The TCA precipitates were filtered onto Millipore HATF plates pre-wetted with 200 µl of 7% TCA+2% sodium pyrophosphate without yeast tRNA. Plates were washed four times with 5% TCA+2% sodium pyrophosphate and filters were dried and coated with Wallac Meltilex A. Scintillant-backed filters were punched onto Fascol marking film, sealed and quantitated using a Wallac 1450 MicroBeta scintillation counter. Alternatively, a Molecular Dynamics Storm System was used; in this case, the filters were not backed with solid scintillant but were quantitated directly.

The results given in Table 2 were measured as the $IC_{50}$ or the concentration of drug compound required to achieve a 50% inhibition of influenza A/WSN virus transcriptass activity.

TABLE 2

| Example Number | $IC_{50}$ (µM) |
|---|---|
| 7 | 0.5 |
| 4 | 0.2 |
| 6 | 0.8 |
| 5 | 1.2 |
| 8 | 0.35 |
| 9 | 0.25 |
| 10 | 0.35 |

The low concentrations of drug compounds required to achieve 50% inhibition of the viral transcriptase activity indicate that the drug compounds of the invention are effective at inhibiting the influenza A/WSN virus transcription process.

EXAMPLE 15

Assay for Antiviral Activity Against Influenza A/WSN

Compounds were evaluated for antiviral activity against influenza A/WSN by plaque reduction in Madin Darby canine kidney (MDCK) cells. Duplicate monolayers of MDCK cells in 6 well plates were washed free of protein-containing media, infected with 50–100 plaque-forming units of virus (0.4 ml volume), and incubated at 37° C. for 60 min. After aspiration of the virus inoculum, a 0.6% agarose overlay (3 ml) containing Eagle minimal essential media, trypsin (8 µg/ml), and the appropriate drug dilution (final concentration of 1% DMSO) was added to the cell monolayer. Plates were incubated at 37° C. in a humidified atmosphere of 5% $CO_2$ in air. After 48 h, monolayers were fixed with glutaraldehyde, stained with 0.1% crystal violet and the plaques were counted. The percentage of plaque inhibition relative to the infected control (no drug) plates were calculated for each drug concentration and the 50% inhibitory concentration ($IC_{50}$) was determined.

The results given in Table 3 were measured as the $IC_{50}$ or the concentration of drug compound required to achieve a 50% inhibition of influenza virus plaque formation.

TABLE 3

| Example Number | $IC_{50}$ (μM) | |
| --- | --- | --- |
| | A/WSN | A/Victoria |
| 7 | 50 | 30 |
| 4 | 50 | 25 |

The plaque reduction results given in Table 2 illustrate that the drug compounds of the invention exhibit antiviral activity against the influenza virus by inhibiting plaque formation by the influenza A/WSN and A/Victoria viruses.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound having the formula:

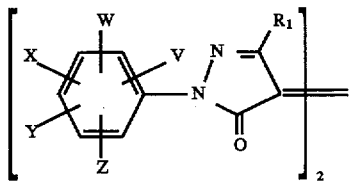

wherein $R_1$ represents a substituent selected from the group consisting of R'CO, COOH, COOR'', CONH$_2$, SO$_2$NH$_2$ and halogen; V represents a substituent selected from the group consisting of COOH, CONH$_2$, COOR''', SO$_2$NH$_2$,

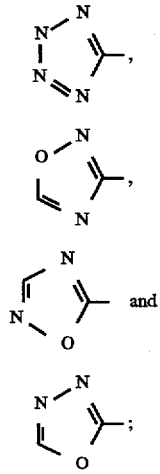

W, X, Y and Z represent the same or different substituents selected from the group consisting of H, alkyl (C$_1$–C$_6$), halogen, CF$_3$, O-alkyl (C$_1$–C$_6$), COOH, CH$_3$S, CH$_3$SO, CH$_3$SO$_2$, COOR'''' and CONH$_2$; R', R'', R''' and R'''' represent the same or different alkyl (C$_1$–C$_6$) substituents, tautomeric forms of said compound, and the pharmaceutically acceptable salts of said compound.

2. A compound having the formula

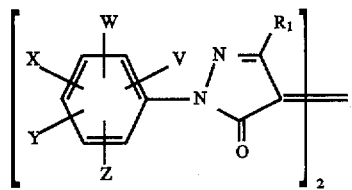

wherein $R_1$ represents CH$_3$CO; V represents a substituent selected from the group consisting of COOH, COOR, and CONH$_2$; W, X, Y and Z represent substituents selected from the group consisting of H, CH$_3$, OCH$_3$, COOH, COOR', CH$_3$S, CH$_3$SO, CH$_3$SO$_2$, CONH$_2$, and Cl, R and R' being the same or different lower alkyl group; tautomeric forms of said compound; and the pharmaceutically acceptable salts of said compound.

3. A compound as claimed in claim 2, wherein V represents 4-COOH; W, X, Y and Z represent H; and $R_1$ represents CH$_3$CO.

4. A compound as claimed in claim 2, wherein V represents 4-COOH; W represents 2-CH$_3$; X, Y and Z represent H; and $R_1$ represents CH$_3$CO.

5. A compound as claimed in claim 2, wherein V represents 4-COOH; W represents 3-Cl; X, Y and Z represent H; and $R_1$ represents CH$_3$CO.

6. A compound as claimed in claim 2, wherein V represents 4-COOH; W represents 2-OCH$_3$; X, Y and Z represent H; and $R_1$ represents CH$_3$CO.

7. A compound as claimed in claim 2, wherein V represents 3-COOH; W, X, Y and Z represent H; and $R_1$ represents CH$_3$CO.

8. A compound as claimed in claim 2, wherein V represents 3-COOH; W represents 4-Cl; X, Y and Z represent H; and $R_1$ represents CH$_3$CO.

9. A compound as claimed in claim 2, wherein V represents 5-COOH; W represents 2-CH$_3$; X, Y and Z represent H; and $R_1$ represents CH$_3$CO.

10. A compound as claimed in claim 2, wherein V represents 4-COOH; W represents 2-Cl; X represents 5-OCH$_3$; Y and Z represent H; and $R_1$ represents CH$_3$CO.

11. A compound as claimed in claim 2, wherein V represents 4-COOH; W represents 3-OCH$_3$; X, Y and Z represent H; and $R_1$ represents CH$_3$CO.

12. A compound as claimed in claim 2, wherein V represents 5-COOH; W represents 2-Cl; X, Y and Z represent H; and $R_1$ represents CH$_3$CO.

13. A pharmaceutical composition for treating influenza virus infection, said composition comprising a compound as claimed in claim 1 in an amount effective to attenuate infectivity of said virus, and a pharmaceutically acceptable carrier medium.

14. A composition as claimed in claim 13 in the form of a tablet with a suitable pharmaceutical carrier or diluent.

15. A composition as claimed in claim 13 comprising from about 5 to about 500 mg of said compound by weight of said composition.

16. A method of treatment of influenza virus infection in a patient in need of said treatment, said method comprising administering to said patient a therapeutically effective amount of a compound as claimed in claim 1.

17. A method as claimed in claim 16, wherein said compound is administered in unit dosage form containing about 0.1 to about 50 mg of said compound per kilogram of patient body weight per day.

18. A method as claimed in claim 17, wherein said unit dosage includes a pharmaceutically acceptable carrier medium.

19. A method as claimed in claim 16, wherein said composition is administered parenterally.

20. A method as claimed in claim 16, wherein said composition is administered orally.

21. A method of preventing influenza virus infection in a host susceptible to said infection, said method comprising administering to said host a prophylactically effective amount of a compound as claimed in claim 1.

22. A method as claimed in claim 21, wherein said compound is administered in unit dosage form containing about 0.1 to about 50 mg of said compound per kilogram of patient body weight per day.

23. A method as claimed in claim 22, wherein said unit dosage includes a pharmaceutically acceptable carrier medium.

24. A method as claimed in claim 21, wherein said composition is administered parenterally.

25. A method as claimed in claim 21, wherein said composition is administered orally.

* * * * *